United States Patent [19]

Yeakey et al.

[11] Patent Number: 4,602,102

[45] Date of Patent: Jul. 22, 1986

[54] PRODUCTION OF ALKYL GLYCOLATES

[75] Inventors: Ernest L. Yeakey; John R. Sanderson, both of Austin, Tex.

[73] Assignee: Texaco Inc., White Plains, N.Y.

[21] Appl. No.: 683,546

[22] Filed: Dec. 19, 1984

[51] Int. Cl.[4] .......................................... C07C 69/675
[52] U.S. Cl. ..................................... 560/179; 568/858
[58] Field of Search ........................ 568/672; 549/430; 560/179

[56] References Cited

U.S. PATENT DOCUMENTS 4,337,371  6/1982  Kollar ................................. 568/852

OTHER PUBLICATIONS

Molera et al., *Chemical Abstracts*, vol. 66, No. 28218p, (1967).

Vetrov et al., *Chemical Abstracts*, vol. 89, No. 146086s, (1978).

Vinokurov, *Chemical Abstracts*, vol. 53, No. 15959i, (1959).

*Primary Examiner*—Natalie Trousof
*Assistant Examiner*—Bruce D. Gray
*Attorney, Agent, or Firm*—Jack H. Park; Kenneth R. Priem

[57] ABSTRACT

It has been surprisingly discovered in accordance with the present invention that when dimethoxymethane is reacted with formaldehyde in the presence of an organic peroxide, the reaction preferentially involves an addition of the formaldehyde to the dimethoxymethane to provide a reaction product containing alkyl glycolates such as methyl glycolate and ethyl glycolate as principle products of the reaction. The alkyl glycolates are useful as raw materials for the manufacture of ethylene glycol.

6 Claims, No Drawings

PRODUCTION OF ALKYL GLYCOLATES

BACKGROUND OF THE INVENTION

1. Technical Field of the Invention

This invention relates to the manufacture of alkyl glycolates. More particularly, this invention relates to a method wherein dimethoxymethane is reacted with formaldehyde in the presence of an organic peroxide under non-acidic conditions to provide alkyl glycolates such as methyl glycolate and ethyl glycolate. The alkyl glycolates are useful as raw materials for the manufacture of ethylene glycol.

2. Prior Art

Kollar U.S. Pat. No. 4,337,371 discloses a method for the preparation of ethylene glycol wherein methanol and formaldehyde are reacted in the presence of an organic peroxide and water to provide ethylene glycol. In a technical article Oyama discloses the free-radical reaction of primary and secondary alcohols such as methanol, 2-propanol, ethanol, 2-butanol and 3-methyl-2-butanol with formaldehyde, and t-butyl peroxide to provide glycols (*J. Org. Chem.*, 30, 2429 (1965). Watanabe et al. in an article in *Bull. Chem. Soc. Jpn.*, 56, 1428–1430 (1983), Vol. 56, No. 5 disclose the reaction of 1,3-dioxolane with electron-deficient alkenes such as diethyl maleate, maleic anhydride, etc. Russian Author's Certificate No. 975,704 (Imashev et al.) discloses a method wherein 1,3-dioxolane is oxidized with molecular oxygen at a temperature of about 10° to 60° C. to provide ethylene glycol monoformate as a principle reaction product.

RELATED COPENDING PATENT APPLICATIONS

Copending coassigned Sanderson et al. U.S. patent application Ser. No. 06/683,549, filed Dec. 19, 1984, now abandoned, discloses a method wherein 1,3-dioxolane is oxidized with molecular oxygen to provide 2-hydroperoxy-1,3-dioxolane.

Copending coassigned Sanderson et al. U.S. patent application Ser. No. 06/683,549, filed Dec. 19, 1984, now U.S. Pat. No. 4,554,364, issued Nov. 19, 1985, discloses a method wherein 2-hydroxyalkyl-1,3-dioxolanes are prepared by the reaction of 1,3-dioxolane with formaldehyde in the presence of a hydroperoxide and an at least sparingly soluble organic metal salt.

Copending coassigned Yeakey et al. U.S. patent application Ser. No. 06/683,546, filed Dec. 19, 1984 discloses a method wherein 1,3-dioxolane is reacted with pararformaldehyde in the presence of an organic peroxide to provide an 2-hydorxymethyl-1,3-dioxolane.

SUMMARY OF THE INVENTION

It has been surprisingly discovered in accordance with the present invention that when dimethoxymethane is reacted with formaldehyde under non-acidic conditions in the presence of an organic peroxide, the preferential reaction products are alkyl glycolates such as methyl glycolate an ethyl glycolate. A minor amount of ethylene glycol is also produced as a minor product of the reaction. The alkyl glycolates are useful as raw materials for the manufacture of ethylene glycol.

DETAILED DESCRIPTION OF THE INVENTION

Starting Materials

The starting materials for the present invention are dimethoxymethane, formaldehyde and organic peroxide.

Formaldehyde may be employed in its conventional form, as an aqueous formalin solution, in "inhibited" methanol solution as paraformaldehyde, or as trioxane.

The organic peroxide employed in the process of the present invention is suitably an organic peroxide having the formula:

$$R-O-O-R'$$

Wherein R and R' are each an alkyl or aralkyl group having 3 to 12 carbon atoms. Organic peroxides which may be employed include, for example, di-tertiarybutylperoxide, tertiary-butyl cumyl peroxide, tertiarybutyl ethylbenzyl peroxide, dicumyl peroxide, etc. The preferred organic peroxide is di-tertiary-butyl peroxide.

Reaction Conditions

The desired products of the present invention are alkyl glycolates which are equimolar addition products of formaldehyde and dimethoxymethane. However, a molar excess of either of the reactants may be used, if desired e.g. about 0.5 to about 5 moles of formaldehyde per mole of dimethoxymethane. Formalin may be used but may hydrolyze dimethoxymethane to methanol and formaldehyde, especially at higher temperatures.

The organic peroxide is suitably in an amount ranging from about 0.01 to about 10 wt. %, based on the 1,3-dioxolane. More preferably, from about 2 to about 5 wt. % of the organic peroxide is used.

The reaction is suitably conducted at a temperature within the range of about 80° to about 250° C., and more preferably, within the range of about 80° to about 150° C.

The reaction is preferably conducted at atmospheric pressure. Superatmospheric or subatmospheric pressures may be used if desired, but there is no particular advantage in doing so.

Reaction times of from about 0.5 to about 10 hours may be employed with satisfactory results. More preferably, the reaction time will be the range of about 1 to about 5 hours.

The reaction can be conducted in inert solvent solution with a solvent such as acetontirile, t-butyl alcohol, monochlorobenzene, benzene, etc. but there is no particular advantage in doing so.

At the end of the reaction, the reaction mixture may be separated into components by any suitable technique such as filtration, distillation, solvent extraction, etc.

SPECIFIC EXAMPLES

EXAMPLE 1

Dimethoxymethane (80 ml), paraformaldehyde (15 g) and di-tert-butylperoxide (3.00 ml) were charged to a 300 cc stainless steel autoclave with magnedrive stirrer. The autoclave was sealed and heated slowly over two hours to 130° C. The autogeneous was ~150 psi. The mixture was then heated to 150° C. over one hour and held at 150° C. for one hour. The autoclave was cooled to ambient temperature and the solid paraformaldehyde filtered from the reaction mixture. The unreacted dimethoxymethane was distilled off at atmospheric pressure to yield 18.1 g of a light yellow oil. The PMR spectrum consisted of a variety of complex bands between 3.3 and 5.3 which were consistent with the following structures:

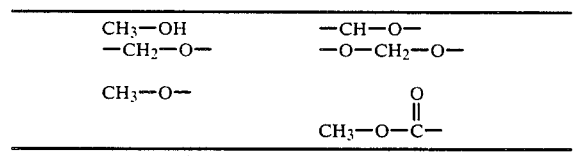

A singlet at 1.2 ppm consistent with the t-butyl group. A singlet at 8.1 ppm consistent with the formate group. The sample was scanned by GC/IR. The results are shown in Table I.

TABLE I

| Area % | Identification or Characteristics |
|---|---|
| 0.25 | Carbon dioxide |
| 37.50 | Water, carbon dioxide, formaldehyde |
| 2.50 | Methanol |
| 0.68 | Methyl formate |
| 0.74 | Ethanol |
| 1.31 | Formic acid and carbon dioxide |
| 1.04 | Dimethoxymethane |
| 2.43 | tert-butanol |
| 2.28 | Hydroxy ketone |
| 5.80 | Ethylene glycol |
| 10.89 | Methyl glycolate |
| 1.96 | Ethylene glycol monoformate |
| 5.57 | 1,3-propanediol |
| 2.93 | Propanediol monoacetate |
| 4.76 | Ethyl glycolate |

EXAMPLE 2

The procedure was the same as in Example 1 except that 10 g paraformaldehyde was used and the mixture was reacted at 130° C. for two hours and 140° C. for one hour. Part of the dimethoxymethane was removed on a rotary evaporator. GC/IR and GC/MS results are shown below.

TABLE II

| Area % | Identification of Characterization | Abundance |
|---|---|---|
| 0.8 | Methane, CO, CO₂ | — |
| 5.2 | Formaldehyde, CO₂ | 68,284 |
| 34.7 | Dimethoxymethane, formaldehyde, CO₂ | 254,432 |
| 2.7 | Acetone + formaldehyde | 35,202 |
| — | Methanol | 4,545 |
| 8.7 | t-butanol | 125,420 |
| 1.0 | Ethanol | 15,086 |
| — | di-tert-butyl peroxide | 58,086 |
| 9.8 | Water | — |
| 13.4 | Methyl glycolate | 64,098 |
| 0.5 | Ethylene carbonate | — |
| 1.0 | Ethylene glycol formate | — |
| 4.4 | Ethylene glycol + ethylene glycol formate | — |
| 5.9 | 1,3-propanediol | 70,021 |
| 3.1 | Ethyl glycolate | — |

EXAMPLE 3

Dimethoxymethane (80 ml), di-tert-butyl peroxide (6.00 ml) and paraformaldehyde (10 g) were charged to a 300 cc stainless-steel autoclave. The autoclave was sealed and heated to 140° C. After 6.0 hours at 140° C., the autoclave was cooled at ambient temperature and the reactor mixture analyzed by GC/MS. The following results were obtained:

TABLE III

| Compound | Ret. Time | Abundance |
|---|---|---|
| Formaldehyde | 1.98 | 6491 |
| Acetaldehyde | 2.04 | 3008 |
| Dimethoxymethane | 2.14 | 252538 |
| Acetone | 2.26 | 49192 |
| Ethyl Formate | 2.30 | 17382 |
| Methanol | 2.38 | 29789 |
| tert-butyl Alcohol | 2.50 | 187280 |
| Ethanol | 2.58 | 37590 |
| di-tert-Butyl Peroxide | 2.98 | 16223 |
| Methyl Glycolate | 8.36 | 43562 |
| Formic Acid | 9.92 | 3912 |
| Ethylene Glycol | 11.66 | 14951 |
| Ethylene Glycol Monoformate | 11.72 | 8742 |

Several unidentified compounds were also present in small quantities.

EXAMPLE 4

The procedure was the same as Example 3, except that the mixture was heated at 160° C. for 6.0 hours. The following results were obtained by GC/MS.

TABLE IV

| Compound | Ret. Time | Abundance |
|---|---|---|
| Formaldehyde | 1.98 | 8874 |
| Acetaldehyde | 2.04 | 2189 |
| Dimethoxymethane | 2.14 | 251060 |
| Acetone | 2.26 | 81520 |
| Ethyl Formate | 2.30 | 29782 |
| Methanol | 2.38 | 41968 |
| tert-butyl Formate | 2.64 | 3812 |
| Methyl Glycolate | 8.38 | 35884 |
| Formic Acid | 9.92 | 3669 |
| Ethylene Glycol | 11.66 | 15086 |
| Ethylene Glycol Monoformate | 11.74 | 7256 |
| 1,3-Propanediol | 13.68 | 19080 |

Several unidentified compounds were also present in small quantities.

EXAMPLE 5

The procedure was the same as Example 3, except that tert-butyl perbenzoate (6.00 ml) was used as the initiator and the mixture was heated at 110° C. for 6.0 hours. The results obtained by GC/MS are shown below:

TABLE V

| Compound | Ret. Time | Abundance |
|---|---|---|
| Formaldehyde | 2.00 | 35792 |
| Methyl Formate | 2.14 | 21051 |
| Dimethoxymethane | 2.18 | 229738 |
| Acetone | 2.28 | 9691 |
| Methanol | 2.40 | 7856 |
| tert-butyl Alcohol | 2.52 | 106722 |
| Ethanol | 2.58 | 8358 |
| Benzene | 3.04 | 31684 |
| Methyl Glycolate | 8.38 | 53048 |
| Ethylene Glycol | 11.64 | 9737 |
| Ethylene Glycol Monoformate | 11.72 | 5258 |
| 1,3-Propanediol | 13.70 | 23249 |
| Benzoic Acid | 20.48 | 21827 |

Several unidentified compounds were also present in small amounts.

The foregoing examples are given by way of illustration and are not intended as limitations on the scope of the present invention, which is defined by the appended claims.

What is claimed is:

1. A method for the preparation of an alkyl glycolate which comprises reacting dimethoxymethane with formaldehyde under non-acidic conditions in the presence of an orgnic peroxode.

2. A method as in claim 1, wherein the organic peroxide is tertiary butyl perbenzoate.

3. A method as in claim 1, wherein the peroxide is ditertiary butyl peroxide.

4. A method which comprises the steps of reacting dimethoxymethane with from about 0.5 to about 5 moles of formaldehyde per mole of dimethoxythane under basic conditions at a temperature within the range of about 80° C. to about 250° C. in the presence of from about 0.01 to about 10 wt. % of an organic peroxide, based on the dimethoxymethane to provide a reaction product comprising alkyl glycolates, including methyl glycolate and ethyl glycolate, as principle products of the reaction.

5. A method as in claim 4, wherein the organic peroxide is tertiary butyl perbenzoate.

6. A method as in claim 4, wherein the organic peroxide is ditertiary butyl peroxide.

* * * * *